(12) United States Patent
Sava Gallis et al.

(10) Patent No.: US 10,320,028 B2
(45) Date of Patent: Jun. 11, 2019

(54) METAL-ORGANIC FRAMEWORK ELECTRODES FOR SODIUM ION BATTERIES

(71) Applicant: National Technology & Engineering Solutions of Sandia, LLC, Albuquerque, NM (US)

(72) Inventors: Dorina F. Sava Gallis, Albuquerque, NM (US); Harry D. Pratt, Albuquerque, NM (US); Travis Mark Anderson, Albuquerque, NM (US); Nicholas Hudak, Washington, DC (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 33 days.

(21) Appl. No.: 15/664,507

(22) Filed: Jul. 31, 2017

(65) Prior Publication Data
US 2018/0053968 A1 Feb. 22, 2018

Related U.S. Application Data

(60) Provisional application No. 62/376,784, filed on Aug. 18, 2016.

(51) Int. Cl.
*H01M 4/00* (2006.01)
*H01M 10/0564* (2010.01)
(Continued)

(52) U.S. Cl.
CPC ....... *H01M 10/0564* (2013.01); *H01M 2/022* (2013.01); *H01M 4/381* (2013.01); *H01M 4/382* (2013.01); *H01M 4/623* (2013.01); *H01M 10/0565* (2013.01); *C01D 13/00* (2013.01); *C07F 15/025* (2013.01); *C08B 11/12* (2013.01); *C08L 1/286* (2013.01); *H01M 2/0222* (2013.01)

(58) Field of Classification Search
CPC ....... C08L 1/286; H01M 2/022; H01M 4/382; H01M 10/0565; H01M 10/0564; C01D 13/00
See application file for complete search history.

(56) References Cited

U.S. PATENT DOCUMENTS 8,252,950 B2   8/2012   Hwang et al.
8,507,399 B2   8/2013   Hwang et al.
(Continued)

OTHER PUBLICATIONS

Pan, H. et al., "Room-Temperature Stationary Sodium-Ion Batteries for Large-Scale Electric Energy Storage", Energy & Environmental Science, 2013, pp. 2338-2360, vol. 6.
(Continued)

*Primary Examiner* — Cynthia H Kelly
*Assistant Examiner* — Monique M Wills
(74) *Attorney, Agent, or Firm* — Kevin W. Bieg

(57) ABSTRACT

A sodium ion battery comprises a cathode having a porous redox active metal-organic framework material. The battery can be an organic electrolyte sodium ion battery wherein the electrolyte comprises a sodium salt dissolved in an organic solvent or mixture of organic solvents. Alternatively, the battery can comprise an aqueous sodium ion battery wherein the electrolyte comprises a sodium salt dissolved in an aqueous solvent. Battery performance is especially related to electrolyte and binder selection.

16 Claims, 16 Drawing Sheets

(51) Int. Cl.
  *H01M 4/38* (2006.01)
  *H01M 4/62* (2006.01)
  *H01M 2/02* (2006.01)
  *H01M 10/0565* (2010.01)
  *C07F 15/02* (2006.01)
  *C08B 11/12* (2006.01)
  *C01D 13/00* (2006.01)
  *C08L 1/28* (2006.01)

(56) References Cited

U.S. PATENT DOCUMENTS

| | | | | |
|---|---|---|---|---|
| 2016/0118688 | A1* | 4/2016 | Nakanishi | H01M 10/0567 429/200 |
| 2017/0012277 | A1* | 1/2017 | Wang | H01M 4/134 |
| 2018/0090751 | A1* | 3/2018 | Xu | H01M 10/054 |

OTHER PUBLICATIONS

Kim, H. et al., "Aqueous Rechargeable Li and Na Ion Batteries", Chemical Reviews, 2014, pp. 11788-11827, vol. 114.

Sun, L. et al., "Electrically Conductive Porous Metal-Organic Frameworks", Angewandte Chemie International Edition, 2016, pp. 3566-3579, vol. 55.

Li, S.-L. et al., "Metal-Organic Frameworks as Platforms for Clean Energy", Energy & Environmental Science, 2013, pp. 1656-1683, vol. 6.

Wang, L. et al., "Metal-Organic Framworks for Energy Storage: Batteries and Supercapacitors", Coordination Chemistry Reviews, 2016, pp. 361-381, vol. 307.

Morozan, A. et al., "Metal Organic Frameworks for Electrochemical Applications", Energy & Environmental Science, 2012, pp. 9269-9290, vol. 5.

Sava Gallis, D. F. et al., "Electrochemical Activity of Fe-MIL-100 as a Positive Electrode for Na-Ion Batteries", Journal of Materials Chemistry A, 2016, pp. 13764-13770, vol. 4.

Decombarieu, G. et al., "In Situ Fe XAFS of Reversible Lithium Insertion in a Flexible Metal Organic Framework Material", Electrochemistry Communications, 2009, pp. 1881-1884, vol. 11.

Fateeva, A. et al., "Synthesis, Structure, Characterization, and Redox Properties of the Porous MIL-68(Fe) Solid", Eur, J. Inorg. Chem., 2010, pp. 3789-3794.

Ferey, G. et al., "Mixed-Valance Li/Fe-Based Metal-Organic Frameworks with Both Reversible Redox and Sorption Properties", Angewandte Chemie International Edition, 2007, pp. 3259-3263, vol. 46.

Li, X. et al., "Shape-Controlled Synthesis and Lithium-Storage Study of Metal-Organic Frameworks Zn4O(1,3,5-benzenetribenzoate)2", Journal of Power Sources, 2006, pp. 542-547, vol. 160.

Ogihara, N. et al., "Organic Dicarboxylate Negative Electrode Materials with Remarkably Small Strain for High-Voltage Bipolar Batteries", Angewandte Chemie International Edition, 2014, pp. 11467-11672, vol. 53.

Saravanan, K. et al., "Lithium Storage in a Metal Organic Framework with Diamondoid topology—a case study on metal formates", Journal of Materials Chemistry, 2010, pp. 8329-8335, vol. 20.

Shin, J. et al., "MIL-101(Fe) as a Lithium-Ion Battery Electrode Material: A Relaxation and Intercalation Mechanism during Lithium Insertion", Journal of Materials Chemistry A, 2015, pp. 4738-4744, vol. 3.

Aubrey, M. L. et al., "A Dual-Ion Battery Cathode via Oxidative Insertion of Anions in a Metal-Organic Framework", Journal of the American Chemical Society, 2015, pp. 13594-13602, vol. 137.

Horcajada, P. et al., "Synthesis and Catalytic Properties of MIL-100(Fe), and Iron(III) Carboxylate with Large Pores", Chem. Commun., 2007, pp. 2820-2822.

* cited by examiner

METAL-ORGANIC FRAMEWORK ELECTRODES FOR SODIUM ION BATTERIES

CROSS-REFERENCE TO RELATED APPLICATION

This application claims the benefit of U.S. Provisional Application No. 62/376,784, filed Aug. 18, 2016, which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to battery technology and, in particular, to metal-organic framework electrodes for sodium ion batteries.

BACKGROUND OF THE INVENTION

Environmental concerns and the limited resources of fossil fuels, in conjunction with energy security needs, have increased the importance of renewable technologies (wind and solar) in the electrical energy landscape. See B. Dunn et al., *Science* 334, 928 (2011). Since renewable energy sources are intermittent, integration with the grid requires reliable energy storage solutions to tailor power generation and supply to demand. See Z. Yang et al., *Chem. Rev.* 111, 3577 (2011). This would allow for a flexible supply of energy, independent of typical peak consumption profiles. Several energy storage technologies for stationary applications have been developed. See Z. Yang et al., *Chem. Rev.* 111, 3577 (2011). Electrical energy storage is well equipped to balance the dynamics of demand and supply, however very few technologies can meet the cost-performance targets required for widespread implementation. See C. J. Barnhart and S. M. Benson, *Energ. Environ. Sci.* 6, 1083 (2013). In addition to cost, safety, reliability via long cycle life, round-trip energy efficiency and minimal maintenance are also important parameters to consider.

Based on these requirements, room temperature Na-ion batteries (NIBs) are becoming increasingly attractive due to: (1) natural abundance and low production cost for Na; (2) reduced safety consideration as compared to traditional rechargeable batteries based on flammable organic electrolytes; and (3) high ionic conductivity, associated with high round-trip efficiency and energy density. See H. Pan et al., *Energy Environ. Sci.* 6, 2338 (2013); and H. Kim et al., *Chem. Rev.* 114, 11788 (2014). In this context, there is a need to develop low cost materials with high energy storage capacity and long cycle life for NIBs.

The vast majority of electrodes for NIBs focus on known materials extensively developed for Li-ion batteries. This is primarily due to the fact that Na- and Li-ion systems have related chemistries, albeit distinct kinetic and thermodynamic properties. See S. Y. Hong et al., *Energy Environ.* 6, 2067 (2013). Metal oxides and polyanionic type compounds have shown the most promising results for NIB electrodes to date. See H. Pan et al., *Energy Environ. Sci.* 6, 2338 (2013). Although significant advancements have been achieved in recent years, there is still a need to implement novel materials with tailorable structures and differentiating reaction mechanisms. See X. Xiang et al., *Adv. Mater.* 27, 5343 (2015); and C. Fang et al., *Adv. Energy Mater.* 6, 1501727 (2016).

In this context, metal-organic frameworks (MOFs) may be attractive battery electrode candidates owing to their high porosity and tunable framework components. Also, their synthesis typically requires low energy input and relatively inexpensive starting materials. MOFs are three-periodic porous materials constructed from single-metal-ions or metal cluster nodes and organic linkers. See S. R. Batten et al., *Pure Appl. Chem.* 85, 1715 (2013). Traditional applications of MOFs relate to gas storage and separations, catalysis, and luminescence, to name a few. See B. Li et al., The *J. Phys. Chem. Lett.* 5, 3468 (2014); M. Eddaoudi et al., *Chem. Soc. Rev.* 44, 228 (2015); D. F. Sava et al., *J. Am. Chem. Soc.* 133, 12398 (2011); D. F. Sava Gallis et al., *Chem. Mater.* 27, 2018 (2015); D. F. Sava Gallis et al., *Chem. Mater.* 28(10), 3327 (2016); J. Lee et al., *Chem. Soc. Rev.* 38, 1450 (2009); Y. Cui et al., *Chem. Rev.* 112, 1126 (2012); D. F. Sava et al., *J. Am. Chem. Soc.* 134, 3983 (2012); and D. F. Sava Gallis et al., *Chem. Mater.* 26, 2943 (2014). Over the course of the past few years, the number of studies that focus on electrical conductivity and electrochemistry-related applications is steadily increasing; however, these reports are still scarce. See L. Sun et al., *Angew. Chem. Int. Ed.* 55, 3566 (2016); S.-L. Li and Q. Xu, *Energy Environ. Sci.* 6, 1656 (2013); L. Wang et al., *Coord. Chem. Rev.* 307, Part 2, 361 (2016); A. Morozan and F. Jaouen, *Energy Environ. Sci.* 5, 9269 (2012); and D. F. Sava Gallis et al., *J. Mater. Chem. A* 4, 13764 (2016). In particular, there are no studies that focus on the electrochemistry of MOFs as battery electrodes.

SUMMARY OF THE INVENTION

The present invention is directed to a sodium ion battery having a cathode comprising a porous redox active metal-organic framework material. The metal-organic framework material comprises a redox active metal center and an organic linker. For example, the redox active metal can comprise V, Cr, Mn, Fe, Co, Ni, or Cu. The organic linker can comprise a heterocyclic aromatic ring, such as benzene, naphtalene, anthracene, pyridine, pyrimidine, imidazole, benzimidazole, pyrazole, purine, thiophene, or benzothiophene. The cathode can further comprise a binder. The battery can be an organic electrolyte sodium ion battery wherein the electrolyte comprises a sodium salt dissolved in an organic solvent or mixture of organic solvents. The sodium salt preferably comprises $NaPF_6$ or $NaClO_4$. Other sodium salts, such as sodium fluoride, sodium tetrafluoroborate, sodium triflate, or sodium triflimide, can also be used. For example, the organic solvent preferably comprises a carbonate solvent, such as propylene carbonate, ethylene carbonate, or dimethyl carbonate. Alternatively, the battery can comprise an aqueous sodium ion battery wherein the electrolyte comprises a sodium salt dissolved in an aqueous solvent. For example, the sodium salt can comprise a sodium halide, sodium sulfate, or sodium phosphate.

As an example of the invention, the performance of an iron (III) carboxylate metal-organic framework electrode was found to be highly dependent on the choice of sodium salt source and the electrolyte system. With aqueous Na-ion batteries, the energy storage capacity is primarily dependent on the binder additive in the composite; the best activity for this MOF is obtained with Nafion as a binder, owing to its hydrophilic and ion conducting nature.

Therefore, consideration of all variables in battery components, and especially electrolyte and binder selection, can lead to greatly improved performances.

BRIEF DESCRIPTION OF THE DRAWINGS

The detailed description will refer to the following drawings, wherein like elements are referred to by like numbers.

FIG. 2(a) is a schematic illustration of medium and large mesoporous cages. The ball represents the largest sphere that can fit inside the cage, considering the van der Waals radii of the nearest atoms. FIG. 2(b) illustrates the trimer arrangement of Fe metal centers. FIG. 2(c) illustrates a 1,3,5-benzenetricarboxylate organic linker. Hydrogen atoms and coordinated water molecules have been omitted for clarity.

FIG. 3(a) is a graph of galvanostatic cycling in 1M $NaPF_6$ in EC:PC, PC, and EC:DMC at 0.1C rate. FIG. 3(b) is a graph of voltage profiles between 4.00-1.5 V (versus $Na^+$/Na) during the $1^{st}$ cycle. FIG. 3(c) is a graph of differential capacity (dQ/dV) of the $1^{st}$ cycle.

FIG. 4(a) is a graph of galvanostatic cycling in 1M $NaClO_4$ in EC:PC:DME at 0.1C rate. FIG. 4(b) is a graph of voltage profiles between 4.00-1.5 V (versus $Na^+$/Na) during the $1^{st}$, $10^{th}$ and $30^{th}$ cycle. FIG. 4(c) is a graph of differential capacity (dQ/dV) of the $1^{st}$ cycle, $10^{th}$ and $30^{th}$ cycle.

FIGS. 13(a)-(b) are graphs of electrodes with Kynar binder. FIGS. 13(c)-(d) are graphs of electrodes with Nafion binder. FIGS. 13(e)-(f) are graphs with binder-free electrodes.

DETAILED DESCRIPTION OF THE INVENTION

MOF Electrodes for Organic Electrolyte Na-ion Batteries

Figure 1:
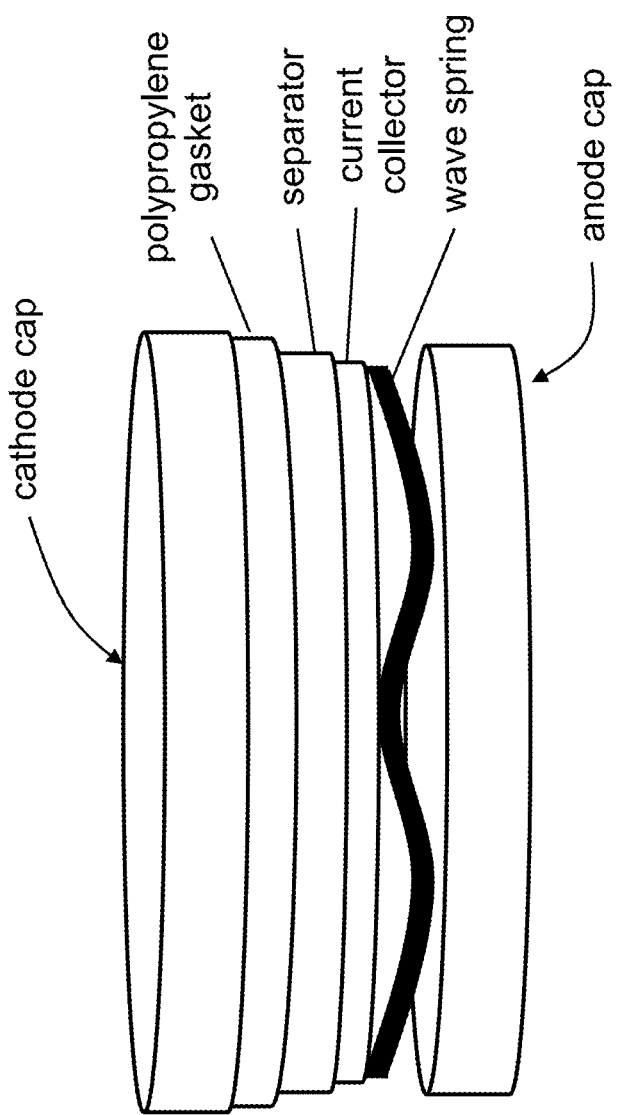
FIG. 1 is a schematic illustration of an assembled coin cell battery.

As an example of an embodiment of the invention, a coin cell NIB was fabricated, as shown in FIG. 1. The coin cell comprises a cathode, an anode, an organic electrolyte, and a porous separator in a sealed housing. According to the invention, the cathode can comprise a porous redox active metal-organic framework (MOF) material, as will be described below. The anode can comprise sodium metal or other sodium anode, such as a carbon-, titanium- or sodium-based anode. The electrolyte is typically absorbed by the electrodes and separator and can be found in the free space of the cell. The electrolyte can comprise a sodium salt dissolved in an organic solvent or mixture of solvents. For example, the organic solvent can comprise a carbonate solvent, such as propylene carbonate, ethylene carbonate, or dimethyl carbonate, or dimethoxyethane. The sodium salt preferably comprises $NaPF_6$ or $NaClO_4$. However, other soluble sodium salts can also be used, such as sodium fluoride, sodium tetrafluoroborate, sodium triflate, or sodium triflimide. The porous separator provides electrode separation and promotes isotropic ion transfer. During charging, an external power supply transports electrons from the cathode into the anode through an external circuit (not shown). Positive sodium ions deintercalate from the cathode and migrate through the ionically conductive electrolyte to the anode, where they recombine with the electrons to form stable sodium atoms. During discharge, these steps are reversed.

MOFs are hybrid inorganic-organic materials constructed from metal nodes and tailorable organic linkers. See H. Furukawa et al., *Science* 341 (2013); and M. Eddaoudi et al., *Chem. Soc. Rev.* 44, 228 (2015). They have inherently 3D porous structures, and have been exploited for a variety of energy and environmental related applications. See S. Ma and H.-C. Zhou, *Chem. Commun.* 46, 44 (2010); J. Lee et al., *Chem. Soc. Rev.* 38, 1450 (2009); K. Sum ida et al., *Chem. Rev.* 112, 724 (2012); Y. He et al., *Chem. Soc. Rev.* 43, 5657 (2014); and D. F. Sava et al., *J. Am. Chem. Soc.* 133, 12398 (2011). Porous MOFs are attractive as battery electrodes due to: (1) the prospect for facile ion insertion and removal during cycling, as slow kinetics is one limiting performance parameter in state-of-the-art metal-oxide layered materials; (2) potential for multi-electron transfer (MOFs can be redox-active via both metal and ligand); and (3) mild synthesis conditions, using abundant precursors. See H. Pan et al., *Energ. Environ. Sci.* 6, 2338 (2013). One significant drawback is the typical low electrical conductivity associated with these materials. However, this can be easily overcome by using electrochemically inert conductive phases, such as carbon or conductive polymers. Several studies have documented the use of MOFs for Li-ion batteries as both negative and positive electrodes. See G. d. Combarieu et al., *Electrochem. Commun.* 11, 1881 (2009); A. Fateeva et al., *Eur. J. Inorg. Chem.* 2010, 3789 (2010); G. Férey et al., *Angew. Chem. Int. Ed.* 46, 3259 (2007); X. Li et al., *J. Power Sources* 160, 542 (2006); N. Ogihara et al., *Angew. Chem. Int. Ed.* 53, 11467 (2014); K. Saravanan et al., *J. Mater. Chem.* 20, 8329 (2010); and J. Shin et al., *J. Mater. Chem. A* 3, 4738 (2015). Additionally, Long and co-workers recently reported the integration of a MOF in a sodium half-cell. See M. L. Aubrey and J. R. Long, *J. Am. Chem. Soc.* 137, 13594 (2015).

Figure 2A:
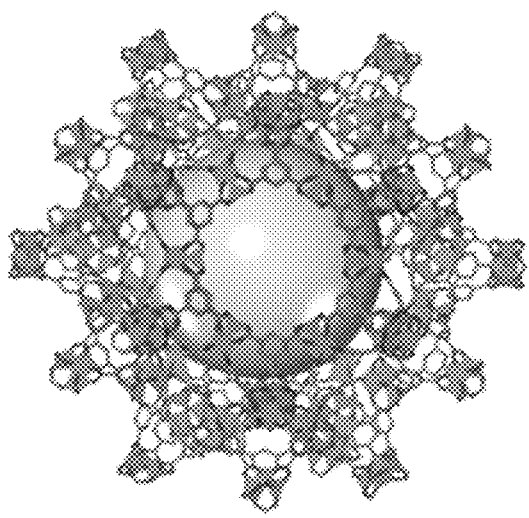
FIGS. 2(a)-(c) show the structural features in Fe-MIL-100.

The MOF material can comprise a redox active metal center and an organic linker. In general, the redox active metal can comprise V, Cr, Mn, Fe, Co, Ni, or Cu, and the organic linker can comprise a heterocyclic aromatic ring, such as benzene, naphtalene, anthracene, pyridine, pyrimidine, imidazole, benzimidazole, pyrazole, purine, thiophene, or benzothiophene. A known MOF with high porosity and chemical stability is Fe-MIL-100; an iron(III) carboxylate having the formula $Fe_3O(H_2O)_2(OH)[C_6H_3(CO_2)_3]_2 \cdot 12H_2O$ and sold commercially as KRICT F100 by Strem Chemicals, Inc. Fe-MIL-100 is used as an example herein to demonstrate the invention, due to its potential to accommodate the intercalation of Na-ions on the basis of the $Fe^{3+}/Fe^{2+}$ redox couple. See P. Horcajada et al., *Chem. Commun.*, 2820 (2007) and U.S. Pat. Nos. 8,507,399 and 8,252,950, which are incorporated herein by reference. A related structure, Fe-MIL-101, was recently exploited as a positive electrode for Li-ion batteries. See J. Shin et al., *J. Mater. Chem. A* 3, 4738 (2015). The structure of the Fe-MIL-100 material is defined by an intricate pore system, based on two types of mesoporous cages of 25 Å and 29 Å in diameter, as shown in FIG. 2(a). The access to the pores is facilitated via pentagonal and hexagonal apertures of ~5.5 Å and ~8.6 Å, respectively. At the core of the framework sits the trimeric arrangement of the Fe metal centers, shown in FIG. 2(b), coordinated by benzenetricarboxylate organic linkers, shown in FIG. 2(c). The coordination sphere of the Fe metal centers is completed by water molecules and, depending of the synthesis conditions, various coordinating anions: for example, $F^-$, $Cl^-$, or $OH^-$.

Cathodes were prepared by mixing a slurry of Fe-MIL-100, SP carbon black, and hexafluoropropylene-vinylidene fluoride copolymer in acetone in a 60:25:15 weight ratio, respectively, and dropcasting the slurry onto a cathode cap. A current collector was made out of 316 stainless steel. The mass of the active material in each coin cell was between 10-15 mg. An electrolyte-soaked borosilicate glass fiber sheet was used as the separator, and sodium metal was used as the anode. Several different electrolytes were used: 1 M $NaPF_6$ in propylene carbonate (PC); 1 M $NaPF_6$ in 1:1 (by weight) ethylene carbonate (EC):PC; 1 M $NaPF_6$ in 1:1 EC:dimethyl carbonate (DMC), and 1 M $NaClO_4$ in 1:1:1 EC:PC: dimethoxyethane (DME). The coin cells were prepared in a dry room (−45° C. dew point, 92 ppm $H_2O$), and tested in ambient air. Cells were cycled at 30° C. using a battery tester between the voltages of 4.0 V and 1.5 V (versus $Na^+/Na$), at a rate of 0.1 C.

Two different Na salts ($NaPF_6$ and $NaClO_4$), four solvent systems (PC, binary mixtures of EC:PC and EC:DMC), and a ternary solvent system incorporating EC:PC:DME) were investigated to identify the most appropriate protocol that would limit interface reactions and allow the highest performance. Electrolyte selection was guided by recent work from Ponrouch et al., where optimized electrolyte blends for Na-ion batteries were identified and discussed in detail. See A. Ponrouch et al., *Energ. Environ. Sci.* 5, 8572 (2012). That work concluded that single solvent systems have the lowest conductivities.

The electrochemical behaviour of Fe-MIL-100 was first investigated in various electrolyte mixtures of $NaPF_6$. This Na salt source was primarily considered as it poses lower safety concerns as compared to $NaClO_4$ salts. In its hydrated form, the theoretical capacity for 1 Na ion intercalation per Fe site is 93 mAh/g. The cathode was cycled against a Na metal counter electrode at a 0.1 C rate (one Na equivalent in 10 hours) in the 4.00-1.5 V (versus $Na^+/Na$) range.

Figure 3A:
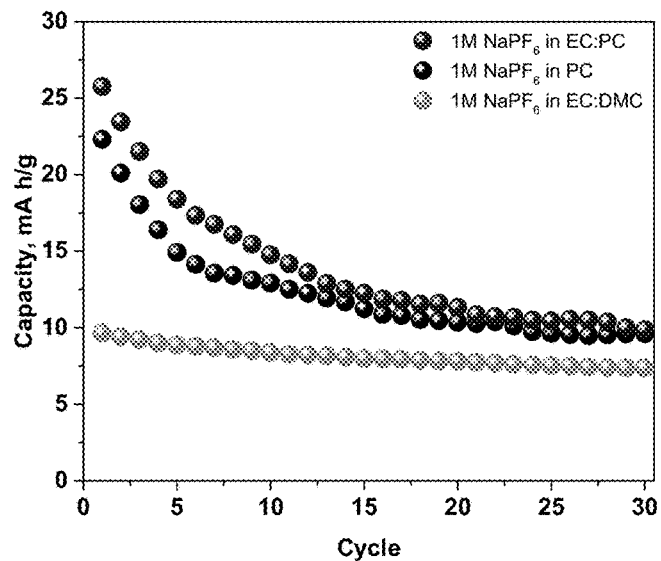
FIGS. 3(a)-(c) show electrochemical characterizations of a Fe-MIL-100 cathode in a $NaPF_6$ electrolyte.

FIG. 3(a) shows the galvanostatic cycling of the Fe-MIL-100 cathode in 1M $NaPF_6$ in EC:PC, PC, and EC:DMC. The specific capacity of the Fe-MIL-100 electrode is strongly dependent on the testing conditions. It is apparent that both the Na salt source and solvent system play a significant role in the electrochemical activity of this material. Similar performance was obtained with the EC:PC and PC solvent mixtures, with ~0.3 Na ions intercalated for each Fe in the first cycle, which correlates with 30% of the theoretical capacity. By cycle 20, a rapid fade was noted, to less than 50% of the initial capacity. This is indicative of a related intercalation and degradation pathway in these two systems. The EC:DMC system accommodates only ~0.1 Na/Fe, and this capacity is mainly retained over the 20 cycles.

Figure 3B:
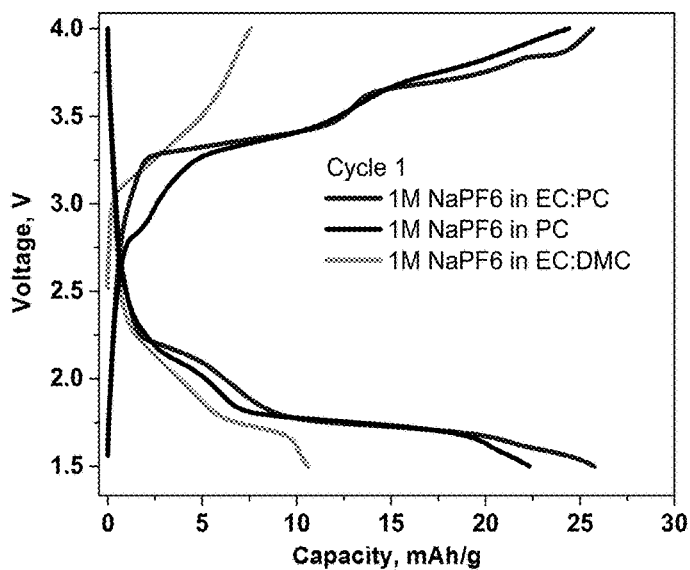

FIG. 3(b) shows the voltage profiles of the three different coin cells during the $1^{st}$ cycle. The voltage profiles of these cells are related, with onsets and plateaus at similar voltages during the first discharge. The potential rapidly reaches 2.25 V at first, and then drops smoothly to 1.75 V. A steady plateau is maintained at this voltage, equivalent to an average intercalation of 0.1-0.26 Na/Fe, upon which the voltage drops sharply to 1.5V. Importantly, most Na ions can be deintercalated upon charging.

Figure 3C:
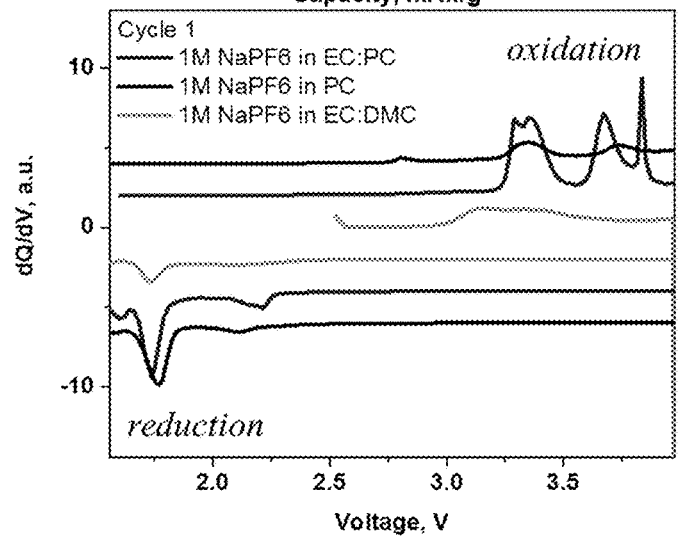

Additional information regarding the electrochemistry of the Fe-MIL-100 cathode can be gathered from the differential capacity plot (dQ/dV), shown in FIG. 3(c). Differential capacity plots were also obtained for the $5^{th}$ and $20^{th}$ cycles (not shown). Related redox pathways in these systems are inferred, with comparable oxidation and reduction peaks, in particular for the PC containing cells. These peaks are not related by symmetry, suggesting that the Na intercalation/deintercalation process proceeds via distinct pathways.

Figure 4A:
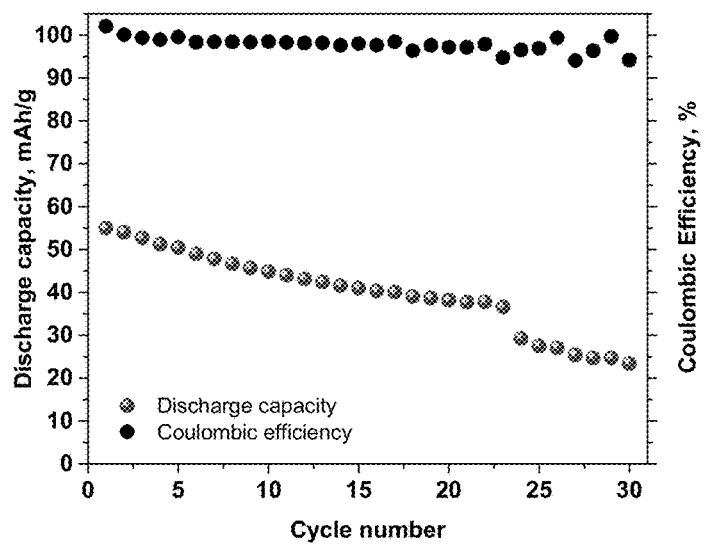
FIGS. 4(a)-(c) show electrochemical characterizations of the Fe-MIL-100 cathode in an $NaClO_4$ electrolyte.

The best performance of the Fe-MIL-100 material as a Na-ion battery cathode was achieved when using a 1M $NaClO_4$ in EC:PC:DME electrolyte mixture. This optimized ternary solvent system was chosen due to the high solubility of the sodium perchlorate. Under these conditions, the capacity reaches ~55 mAh/g at a 0.1 C rate in the first discharge cycle, as shown in FIG. 4(a). This represents the intercalation of ~0.6 Na ions per Fe metal centre and closely matches the capacities observed in other Fe-based MOFs, previously studied as Li-ion battery cathodes: Fe-MIL-101 (0.62 Li/Fe) and Fe-MIL-53 (0.62 Li/Fe). See J. Shin et al., *J. Mater. Chem. A* 3, 4738 (2015); and G. Férey et al., *Angew. Chem. Int. Ed.* 46, 3259 (2007). Similar to the profile of the coin cells using $NaPF_6$, the capacity fades quickly, reaching ~50% of the initial capacity by cycle 30. Importantly, the diminished performance is not accompanied by a decrease in the Coulombic efficiency (CE).

Figure 4B:
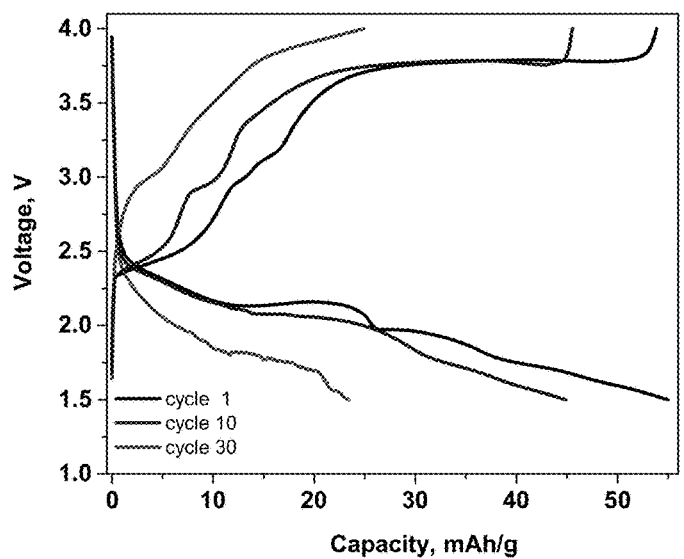
Figure 4C:
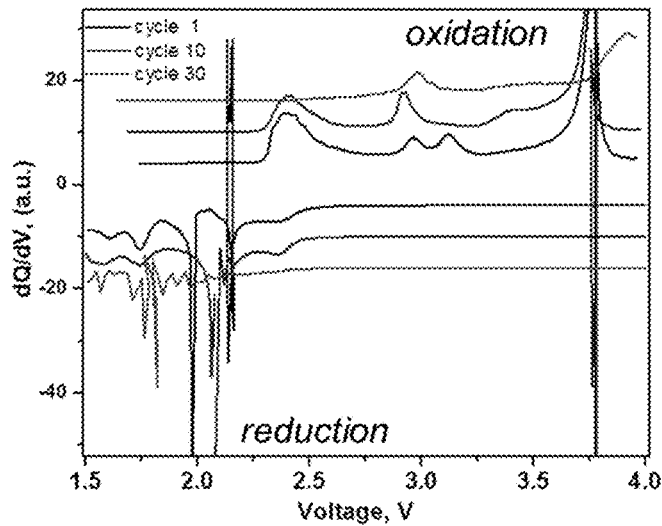

Voltage profiles and differential capacity plots after the $1^{st}$, $10^{th}$ and $30^{th}$ cycles are shown in FIGS. 4(b) and 4(c), respectively. Distinct electrochemical profiles are noted with progressive cycling, suggesting different, but fully reversible Na intercalation/deintercalation pathways, as indicated by the CE. In particular, multiple reduction and oxidation peaks, as shown in FIG. 4(c), may indicate several sites for intercalated Na ions. The fade in capacity correlates with the changes in the oxidation/reduction profiles; as such, some peaks decrease in intensity or completely disappear with cycling.

Ex-situ structural characterization was performed to gather a fundamental understanding of the degradation pathways in this cathode material. This included powder X-ray diffraction via synchrotron data, as well as pair distribution function (PDF) analyses of the as-made electrodes and electrodes stopped at various points during the cycling: after the $1^{st}$ discharge, $1^{st}$ charge, and after the $10^{th}$ and $30^{th}$ cycles (where the final state of the sample is in a charged state).

Figure 5:
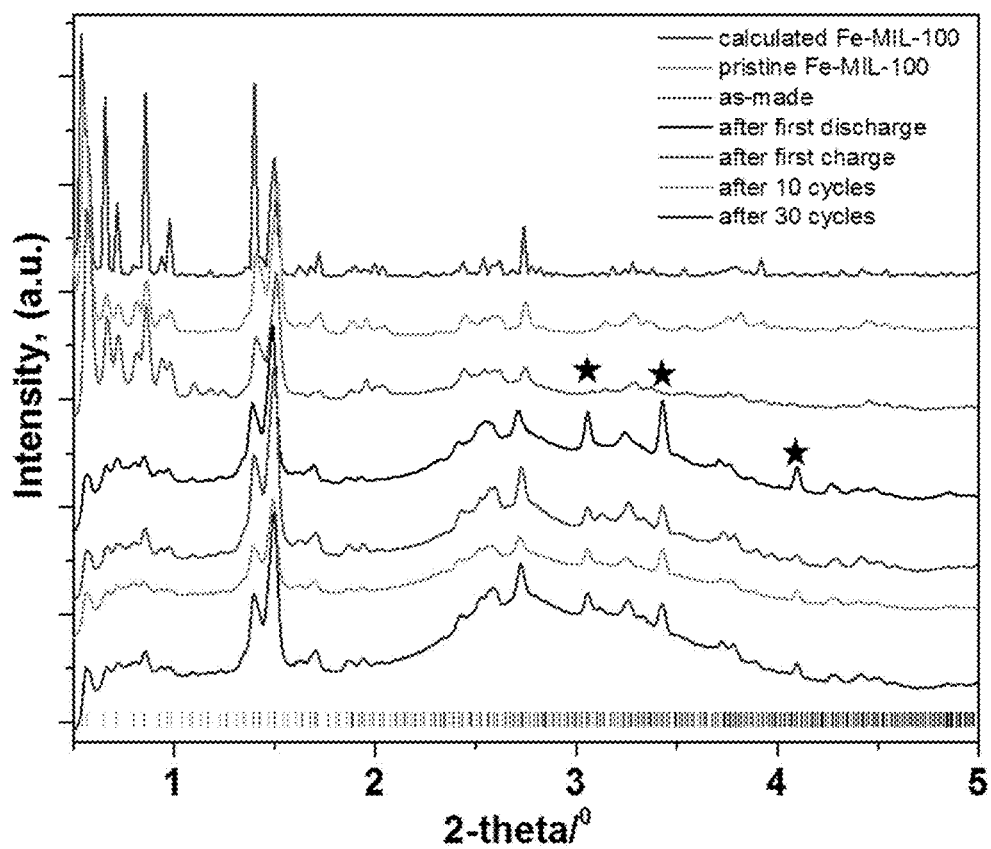
FIG. 5 is a graph of synchrotron X-ray diffraction data for calculated and pristine Fe-MIL-100, and as-made and cycled Fe-MIL-100 electrodes. Data have been offset for clarity; tick marks represent predicted d-spacing values for the calculated reflections.

As shown in FIG. 5, the diffraction data for the cycled samples show that peaks corresponding to the MIL-100 phase are retained following cycling. Following the initial discharge, the relative intensity of the peaks at low angle are reduced—this is the largest change in the diffraction features for MIL-100, the peaks do not change substantially with subsequent cycling. Diffuse contributions to the scattering data, from a poorly-ordered amorphous phase, are increased for the cycled samples. This diffuse scattering is characterized by broad features centred at 2.7 and 3.2°. There are several additional sharp peaks from a new crystalline phase at 3.1°, 3.4° and 4.2° (indicated with a star in FIG. 5), identified as $NaClO_4$ salt. This is to be expected, since the electrodes were not washed prior to data collection.

Figure 6A:
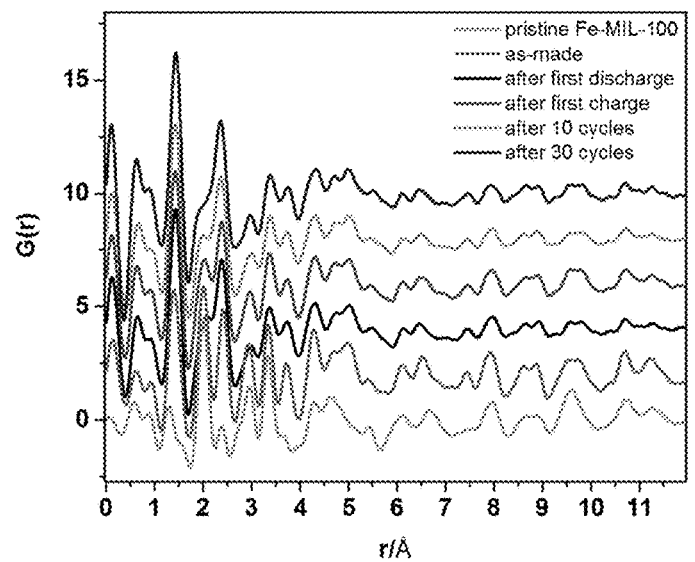
FIG. 6(a) is a graph of high r PDF data.
Figure 6B:
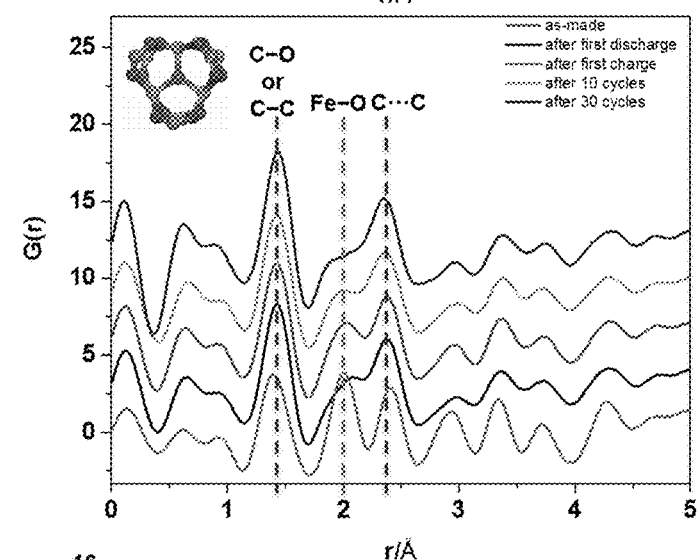
FIG. 6(b) is a graph of low r PDF data.
Figure 6C:
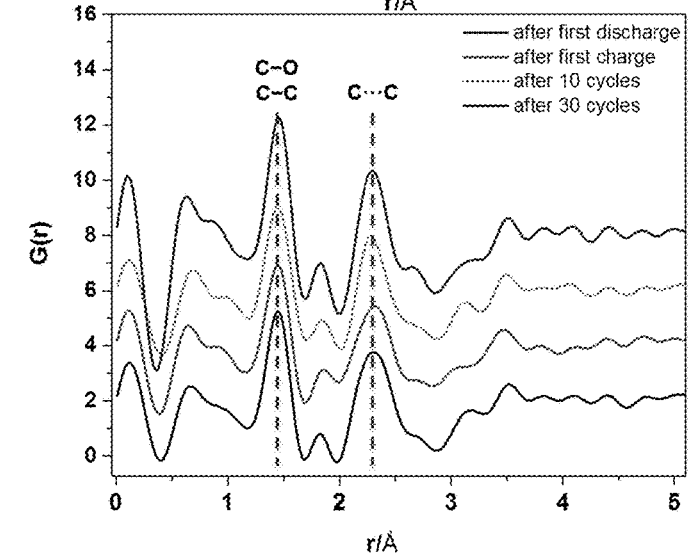
FIG. 6(c) is a graph of the differential analysis of the PDFs (subtracting the PDF of the as-made electrode from the cycled samples), showing that changes following cycling are predominantly due to formation of organic polymeric phases.

The PDF data provides structural insights into both crystalline and non-crystalline components of the sample as a weighted histogram of atom-atom distances within the electrode. The features in the PDF at long distances, reflective of ordered crystalline phases within the electrode (i.e., Fe-MIL-100), are largely retained following cycling, as shown in FIG. 6(a). By contrast, large changes are evident in the local bonding reflected in the low r-region of the PDF, as shown in FIG. 6(b). While overlapping distances make it difficult to unambiguously assign features in the PDF to individual atom-atom correlations, applying a differential analysis provides several clear insights, as shown in FIG. 6(c). The dominant changes to the atom-atom features with cycling involves the formation of additional bonds at ~1.4 Å and ~2.3 Å. These are characteristic of C—O/O and 1,3-C . . . C distances respectively in a poorly-ordered phase. The peak at 2.0 Å, which is reflective of the Fe—O bond within the nodes of the MIL-100 lattice evident in the as prepared electrode, has low intensity relative to this amorphous organic component following cycling.

The diffraction and high r features in the PDF data indicate that the MIL-100 structure is retained throughout Na charging and discharging. The increasing diffuse contribution to the diffraction data and the increased intensity of features in the PDF attributable to amorphous carbons/organics indicates the presence of an additional phase or component in the electrode following cycling. This may be due to electrolyte decomposition reactions. A reduced intensity of the low angle diffraction peaks in porous MOFs is consistent with filling of the pores. This suggests that the newly formed amorphous phase occupies the pores of the MIL-100 framework. Importantly, these extra-framework components can be removed when washing the cycled electrodes with DME. A significant reversion of the low angle peak intensities and reduced diffuse background was observed with washing, confirming the structure is maintained with cycling.

The characteristics described above help identify the complex interplay between the multiple variable parameters in these systems. Among those, the material state (hydrated vs. dehydrated), and the ratio of active material to the carbon conductive phase and binder were some of the most critical. For example, the best results were obtained on the hydrated version of the material, in a 60:25:15 weight ratio.

With regards to the electrolyte systems using a $NaPF_6$ salt source, the performance was clearly affected by the identity of the electrolyte and/or electrolyte mixtures. This is consistent with previous electronic structure calculations which have shown that the Fe oxidation state reduction is dependent on the coordinating anion. See J. Shin et al., *J. Mater. Chem. A* 3, 4738 (2015). Specifically, a coordinated DMC molecule to the Fe is two times more likely to facilitate the reduction of $Fe^{3+}$ to $Fe^{2+}$, as compared to when a Cl anion is bound in the same configuration. The electrolyte performance dependence can be explained by the possibility of various/mixed anion coordination at the trimer centres. These would displace the hydroxyl groups, thus resulting in a higher or lower propensity for the reduction of $Fe^{3+}$. Additionally, the presence of water most likely affects the overall performance of the $NaPF_6$ coin cells as compared to the $NaClO_4$ system. HF is a common by-product and is known to adversely affect the performance of batteries utilizing $PF_6$ salts. See D. Aurbach et al., *J. Electrochem. Soc.* 147, 1322 (2000).

The degradation pathway of the best performing $NaClO_4$ based system can be inferred from the electrochemical profile in combination with the ex situ X-ray structural analysis of the cycled electrodes. Multiple reduction and oxidation peaks in the differential capacity plot may indicate several sites for intercalated Na ions. A similar profile was noted for the related Fe-MIL-101 Li cathode study, which is based on the same trimeric secondary building unit. Several of these peaks either decrease in intensity or completely vanish upon cycling, suggesting a reduced redox activity of the Fe metal centre, as well as less availability for Na insertion sites. This can be further correlated with the increase in the guest population inside the cages, as suggested by both X-ray synchrotron diffraction and PDF studies. The presence of the extra carbonaceous species inside the pores upon cycling is likely resulting from electrolyte decomposition and from parasitic reactions between electrodes and electrolyte.

Lastly, studies of nanosized particles (in the 25-50 nm range) of the Fe-MIL-100 material showed that the performance can be improved to approach the theoretical capacity, 93 mA/g. Similar observations have been previously noted with in both Li cells and NIBs. See P. Poizot et al., *Nature* 407, 496 (2000); and S. Komaba et al., *J. Electrochem. Soc.* 157, A60 (2010).

Although porosity and redox propensity are important selection criteria, these two requirements alone are not sufficient. In particular, the electrolyte and sodium salt source play a critical role in the performance of Fe-MIL-100 as a cathode for NIB. The degradation pathway in the battery performance is mainly associated with inaccessibility of active sites for Na intercalation and sluggish kinetics due to pore filling with carbonaceous species as a result of electrolyte decomposition.

The crystallinity is mainly preserved in Fe-MIL-100 with progressive cycling, suggesting that careful consideration of all variables in battery components, and especially electrolyte selection can lead to improved performances. The particle size effects the performance of Fe-MIL-100 as a cathode for NIB. Other solvent systems, including aqueous-based, can also be used, as will be described below. Water meets the cost and safety requirements over extended use needed in large-scale energy storage.

MOF Electrodes for Aqueous Na-ion Batteries

Figure 2C:
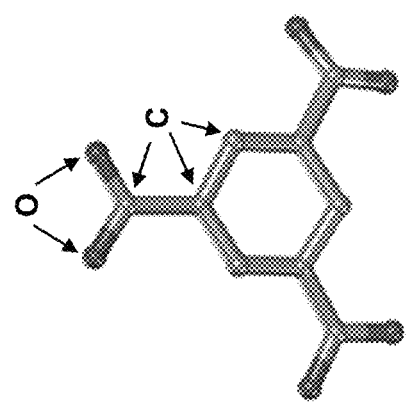
Figure 2B:
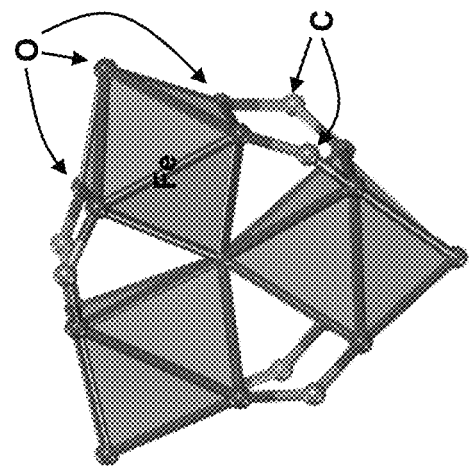

The invention is further directed to the use of MOFs as electrodes for aqueous NIBs. As an example of the invention, the electrochemical activity of Fe-MIL-100 was also examined as an electrode for an aqueous NIB. See P. Horcajada et al., *Chem. Commun.* 27, 2820 (2007). This material choice was guided by its robustness in water, a prerequisite that few potentially redox-active MOFs can meet, and its electrochemical activity in a variety of organic solvent electrolytes for a NIB, as described above. As shown in FIGS. 2(a)-(c), Fe-MIL-100 is constructed from Fe-based trimer building blocks, linked by 1,3,5-benzenetricarboxylate struts to generate an open framework based on mesoporous cages of 25 Å and 29 Å in diameter. The material is redox active via the $Fe^{3+}/Fe^{2+}$ redox couple.

Figure 7:
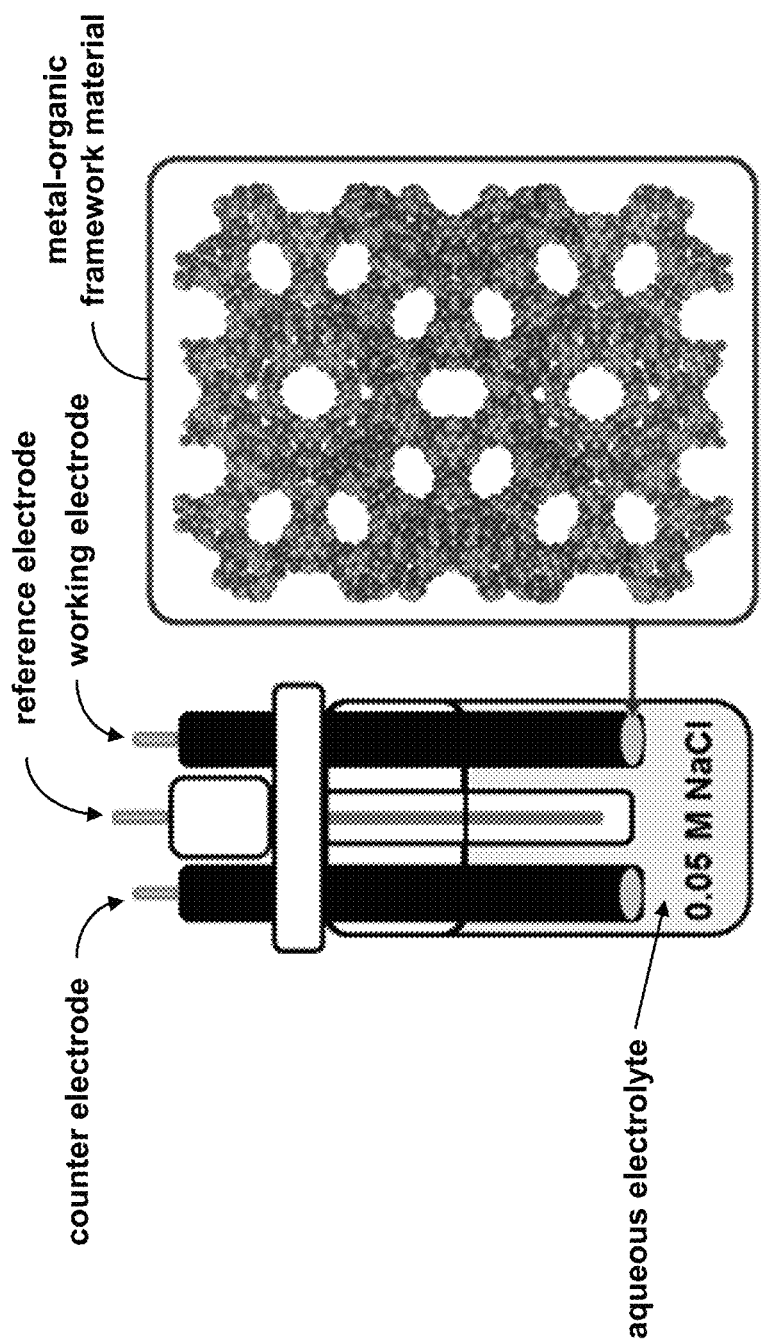
FIG. 7 is a schematic illustration of an electrochemical cell comprising a MOF electrode in a 0.05 M NaCl/water electrolyte.

As shown in FIG. 7, electrochemical characterization was conducted on an electrochemical cell through cyclic voltammograms (CV) and galvanostatic cycling (GC) with a potentiostat with potential limitations. Working and counter electrodes were made using BASi® stationary voltammetry electrodes with 6.4 mm outside diameter (OD) and 1.6 mm diameter glassy carbon. All tests were conducted in the three-electrode cell with two glassy carbon and one Ag/AgCl reference electrode with 0.05 M NaCl in water as the electrolyte. Other water-soluble sodium salts, such as sodium halides, sodium sulfates, and sodium phosphates can also be used as electrolytes.

Traditionally, composite fabrication and particle size are critical parameters to monitor in the performance of battery electrodes. See Y. Wang et al., *Nanoscale* 2, 1294 (2010); and A. Magasinski et al., *ACS Appl. Mater. Interfaces* 2, 3004 (2010). Therefore, the interface between the electrode and electrolyte is important in the overall performance of Fe-MIL-100 as an electrode for aqueous NIBs. In particular, binder additives (e.g., Nafion, Kynar and binder-free) affect the composite's electrochemical activity (Nafion is a sulfonated tetrafluoroethylene based fluoropolymer-copolymer. Nafion® is a registered trademark of E. I. Du Pont De Nemours and Company. Kynar is a hexafluoropropylene-vinylidene fluoride copolymer. Kynar® is a registered trademark of Arkema Inc.). Kynar-containing working electrode mixtures were based on 60:20:20 wt. % of active material (Fe-MIL-100): sp carbonblack: Kynar. For the binder-free electrodes, that ratio was 60:20 wt. % active material (Fe-MIL-100): sp carbonblack. The slurry mixtures were drop cast onto the electrodes with carbon paper, which was a necessary intermediate in the aqueous system in order for the slurry to adhere to the electrodes. For experiments involving Nafion, no carbon paper was used due to Nafion's adhesive properties onto the electrodes, while the wt. % mixture of active materials to carbon was maintained as described above.

Although it is common in the aqueous sodium-ion battery literature to test active materials against a sodium-free counter electrode (such as Pt or Zn for example), the absence of sodium in the counter electrode leads to side reactions such as metal dissolution/plating and/or electrolyte degradation ($H_2$ and/or $O_2$ evolution). See S. I. Park et al., *J. Electrochem. Soc.* 158, A1067 (2011). In either case, the composition of the electrolyte is modified by the side reactions at the counter electrode. Counter electrodes containing the relevant cation involved in the electrochemical system have been shown to be important for achieving high performance in aqueous batteries. See R. Ruffo et al., *Electrochem. Commun.* 11, 247 (2009). Therefore, MOF-based electrodes were first sodiated to be used as counter electrodes in later experiments. The sodiation was achieved in a three electrode cell consisting of MOF-based electrodes prepared as working electrodes, Pt counter electrodes, and Ag/AgCl reference electrodes. This procedure was modified from previously published work. See C. D. Wessells et al., *Nano Lett.* 11, 5421 (2011). The counter electrode was intentionally made to be 2-5 times the mass of the working electrode so that any electrochemical activity within the cell left the counter electrode relatively unaltered. All values for the electrochemical characterizations are reported against SHE.

Figures 8A, 8B:
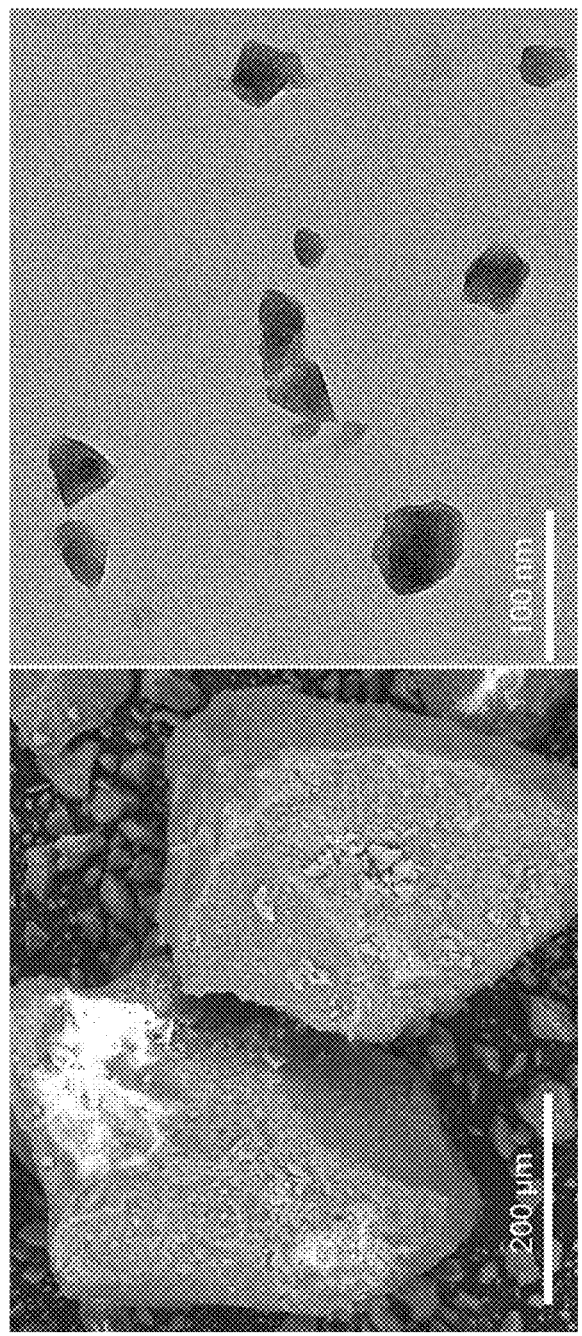
FIG. 8(a) is a scanning electron microscopy (SEM) image of micro-Fe-MIL-100.
FIG. 8(b) is a transmission electron microscopy (TEM) image of nano-Fe-M IL-100.

Electrode composition/binder (e.g., Kynar, Nafion, and binder-free) was first examined as function of particle size (micro- vs nano-) to better correlate structural features with this material's electrochemical activity in aqueous electrolytes. Two different particle sizes of the Fe-MIL-100 material were used, micro- and nano-sized, as seen in FIGS. 8(a) and FIG. 8(b), respectively. Micro-Fe-MIL-100 (Iron III 1,3,5-benzenetricarboxylate, hydrate, porous) was purchased under the chemical name of KRICT F100 from Strem Chemicals. The synthesis of nano-Fe-MIL-100 was adapted from a previously published method. See A. Garcia Márquez et al., *Eur. J. Inorg. Chem.* 32, 5165 (2012). There is a wide size distribution for the large particles, 25-200 µm, whereas the nanoparticles are more homogeneous, with sizes in the 20-50 nm range.

Figure 9A:
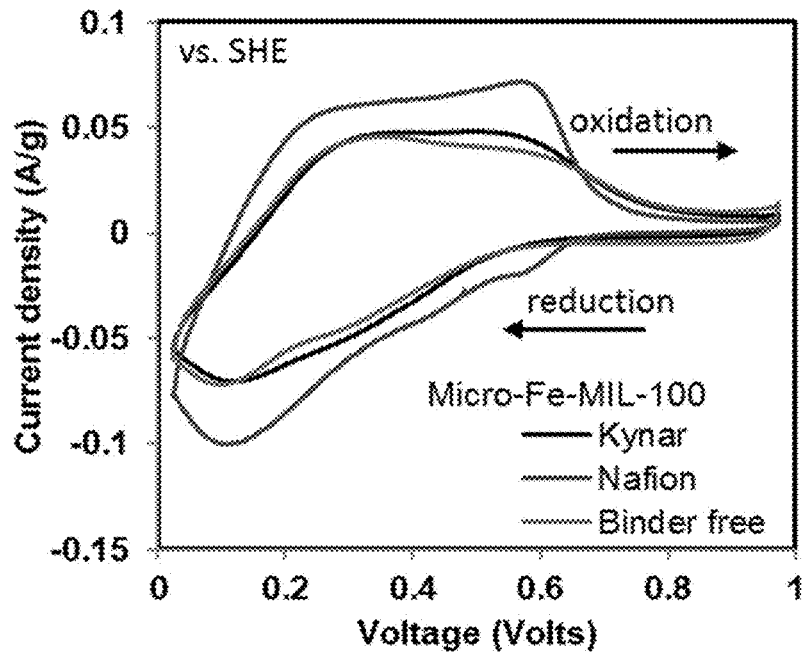
FIG. 9(a) is a graph of a first cycle cyclic voltammogram of micro-Fe-MIL-100 at a scan rate of 1 mV/s with a 0.05M NaCl in water electrolyte.
Figure 9B:
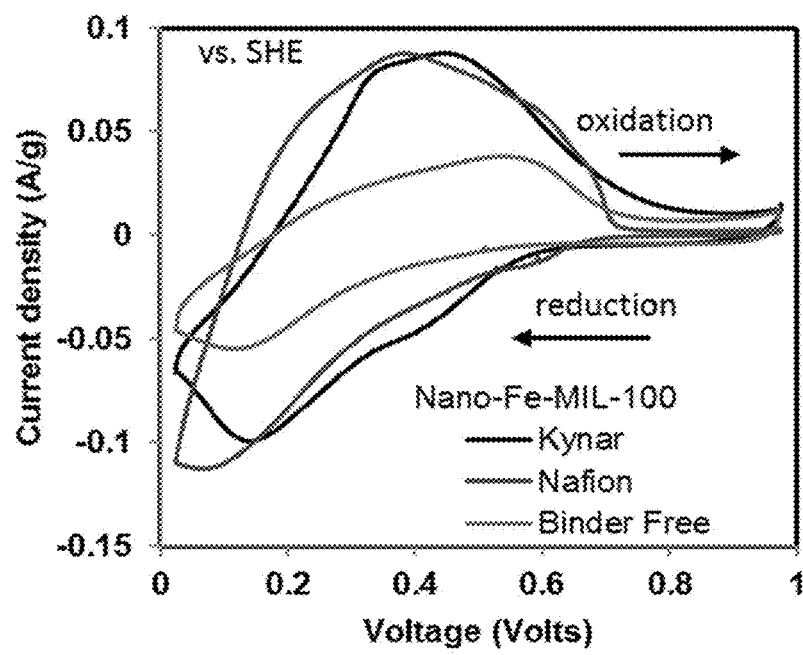
FIG. 9(b) is a graph of a first cycle cyclic voltammogram of nano-Fe-MIL-100.

As shown in FIG. 9(a), the initially desodiated micro-Fe-MIL-100 was first reduced and then oxidized. The Nafion-bound electrode exhibits larger reduction and oxidation current densities than the other binder systems and has a well-defined oxidation peak at ~0.55 V and a smaller peak at ~0.2 V. All curves exhibit strong reductive peaks at ~0.1 V and shoulders at higher potentials. The Kynar-bound and binder-free electrodes share similar characteristics, but exhibit lower current densities. As shown in FIG. 9(b), the nano-Fe-MIL-100 CVs generally show similar activity to micro-Fe-MIL-100. However, nano-Fe-MIL-100 shows higher peak current densities than micro-Fe-MIL-100 for the Kynar- and Nafion-bound electrodes. In conjunction, the oxidation peaks shift such that they merge closer together for nano-Fe-MIL-100. Also, the binder-free nano-Fe-MIL-100 electrode exhibits lower current density and less distinctive peaks than all other samples.

Figure 10A:
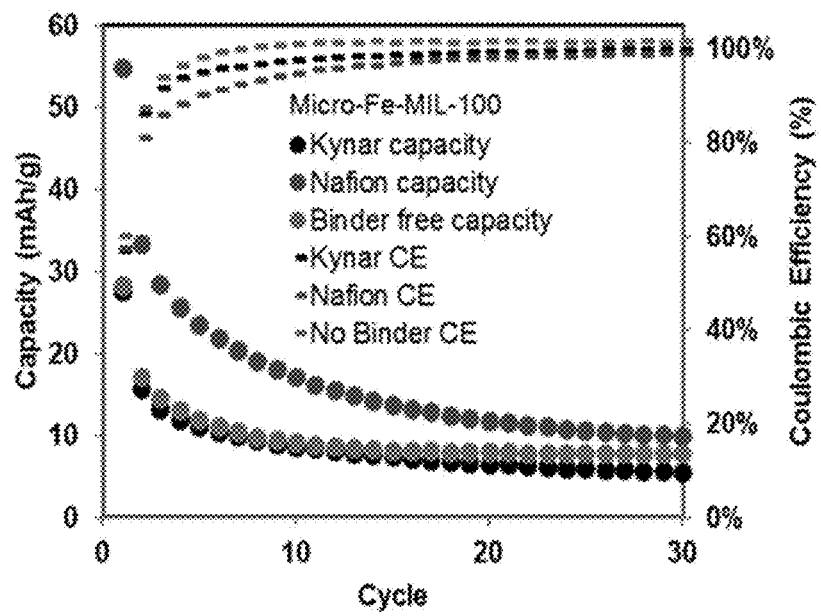
FIG. 10(a) is a graph of cycle life (reduction values) and Coulombic efficiency of micro-Fe-MIL-100 at a C/3 rate in a 0.05 M NaCl/water electrolyte.
Figure 10B:
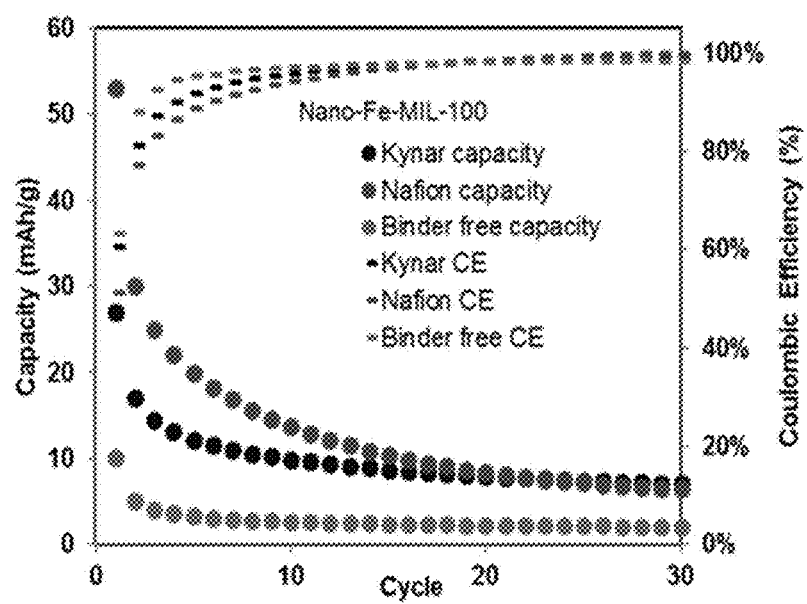
FIG. 10(b) is a graph of cycle life (reduction values) and Coulombic efficiency of nano-Fe-MIL-100.
Figure 11:
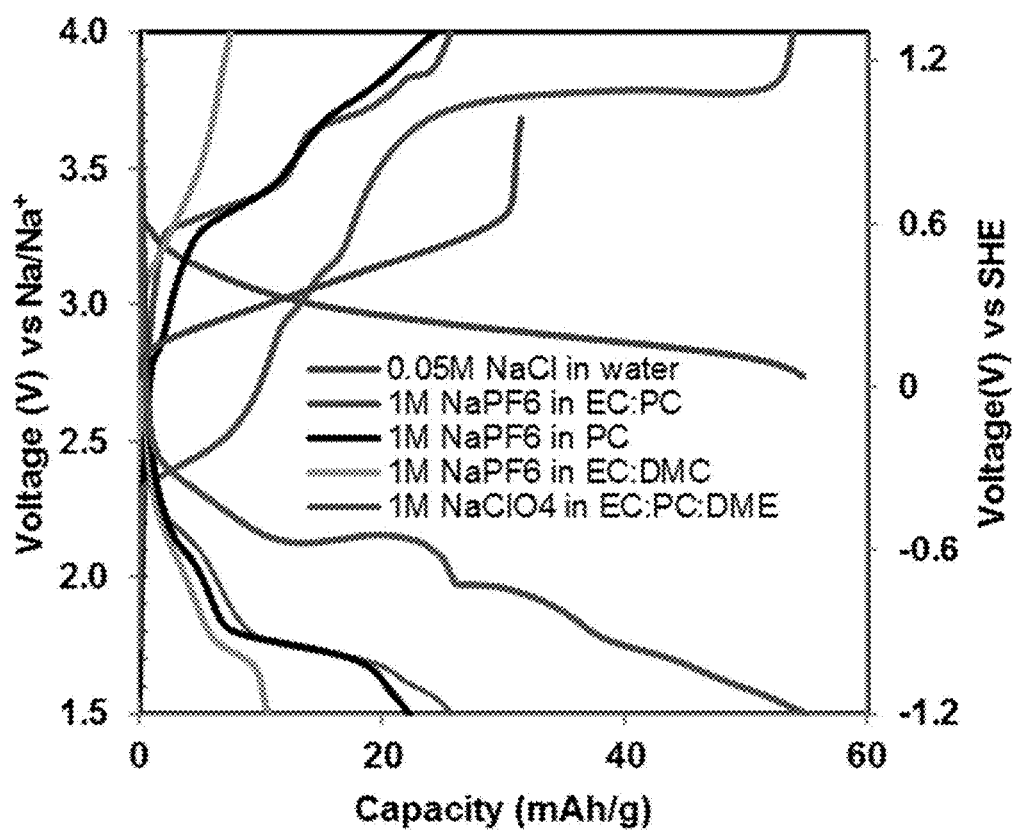
FIG. 11 is a graph of voltage profiles versus $Na^+$/Na during the $1^{st}$ cycle in organic vs aqueous electrolytes.

The Na storage capacity of Nafion, Kynar and binder-free micro- and nano-Fe-MIL-100 electrodes was examined. The theoretical capacity of Fe-MIL-100 is 93 mAh/g, when considering $Fe^{3+}/Fe^{2+}$ the electrochemically active redox couple. FIGS. 10(a) and 10(b) show the sodium storage capacity over 30 cycles for micro-Fe-MIL-100 and nano-Fe-MIL-100, respectively, cycled at a C/3 rate. All cells exhibit the highest reduction capacities in the first cycles, which drop sharply and reach steady values after ~10-20 cycles. For the best performing system, Nafion-bound micro-Fe-MIL-100, the first cycle capacity is of 55 mAh/g, representing ~60% of the theoretical capacity. This storage capacity is the same as that measured on the same MOF active material in the coin cell configuration using an organic electrolyte, as described above. The voltage profiles during the first cycle in both the aqueous and organic electrolytes are shown in FIG. 11. There are several differences between the electrochemical behavior in these two electrolyte systems. First, the potential where electrochemical activity occurs is higher in the aqueous electrolyte. Second, the electrochemical activity occurs in distinct, flat plateaus in the organic electrolytes but the plateaus slope much more gradually in the aqueous electrolyte. This suggests that different mechanisms might be responsible for the capacity in different electrolytes, including: (1) unique redox sites with different energies; (2) different Na solvation structures, which may favor access to distinct sites; and (3) distinct intercalation mechanisms.

A comparison to other MOFs evaluated as electrodes reveals similar results, indicating limitations to the storage of charge in the MOFs studied thus far in the literature. See D. F. Sava Gallis et al., *J. Mater. Chem. A* 4, 13764 (2016); G. Férey et al., *Angew. Chem. Int. Ed.* 46, 3259 (2007); A. Fateeva et al., *Eur. J. Inorg. Chem.* 24, 3789 (2010); and J. Shin et al., *J. Mater. Chem. A* 3, 4738 (2015). Consistent with the CV data, the micro-Fe-MIL-100 Nafion-bound electrode shows higher capacity than the Kynar-bound and binder-free electrodes, as shown in FIG. 10(a). However, by cycle 30, the Nafion-bound electrode shows similar capacity as the other binder systems. Nano-Fe-MIL-100 performed similarly to micro-Fe-MIL-100 despite variations in peak current densities and peak locations evident in the CV, as shown in FIG. 10(b). Consistent with the CV, the binder-free nano-Fe-MIL-100 exhibited the lowest capacity.

In general, particle size has little effect on the electrochemistry, indicating that the capacity limitations at the rates studied here are not related to the ionic and electronic conductivity limitations that sometimes plague materials with micron-sized particle morphologies. See Y. Wang et al., *Nanoscale* 2, 1294 (2010).

Conversely, the composition of the electrode and, in particular, the binder, greatly impacts the capacity in the early cycles of micro- and nano-Fe-MIL-100 alike. For both particle systems, Nafion exhibits the highest charge storage capacity, particularly during the first 10 cycles. The improved performance of the Nafion-bound cells relates to the inherent hydrophilic nature of Nafion, which allows it to be used effectively in other aqueous systems, such as fuel cells and in electrocatalytic water splitting. See K. Broka and P. Ekdunge, *J. Appl. Electrochem.* 27, 117 (1997); and K. Meyer et al., *Energy Environ. Sci.* 8, 1923 (2015). Its hydrophilicity likely enhances wetting of the electrode allowing a more favorable interfacial interaction between the electrolyte and composite electrode. Additionally, whereas most binders function to simply hold together a composite electrode, Nafion is an ion transporter and can act as an electrolyte in aqueous systems. Specifically, while Nafion typically transports protons in aqueous systems such as fuel cells, it is also capable of transporting Na ions. See H. L. Yeager et al., *J. Electrochem. Soc.* 127, 303 (1980). Other hydrophilic binders, such as sodium carboxymethyl cellulose, can also be used with the invention.

Conversely, Kynar is a hydrophobic binder, which impedes wetting of the electrode and affects how the ions and water molecules arrange at the interface between the electrolyte and composite electrode. This has a noticeable effect on the performance of the Kynar-bound electrodes, clearly less effective than the Nafion-bound cells. Other hydrophobic binders, such as polytetrafluoroethylene (PTFE), can also be used with the invention.

The binder-free systems show the poorest electrochemical activity. In particular, the binder-free nano-Fe-MIL-100 shows much lower capacity in all cycles than binder-free micro-Fe-MIL-100, as well as all other systems with binder. This is due to the fact that the smaller particle sizes are more difficult to adhere together without binder, as opposed to larger particles. Also, many more particle-to-particle connections are occurring in this system. In this case, it is likely that some of the active material lacks a low-impedance connection to the current collector. Poor electrical connections and isolation of some particles can lead to lower capacity.

Although the highest capacities are reached in the initial cycles, the Coulombic efficiency (CE) exhibits the opposite trend for all binder systems; while starting at 60%, it increases with cycling to near 100% near cycle 20, as shown in FIGS. 10(a) and 10(b). Here, CE is defined as the oxidation (desodiation) charge capacity divided by the reduction (sodiation) charge capacity multiplied by 100 to convert to percentage. This effectively indicates the percentage of electrons consumed during sodiation that can be recovered upon desodiation. CE is typically defined this way when beginning with initially desodiated/delithiated materials. Si anodes serve as an example for which CE is defined as discharge capacity (oxidation or delithiation charge) divided by charge capacity (reduction or lithiation charge). See C. K. Chan et al.,*Nat. Nano* 3, 31 (2008).

Figure 12:
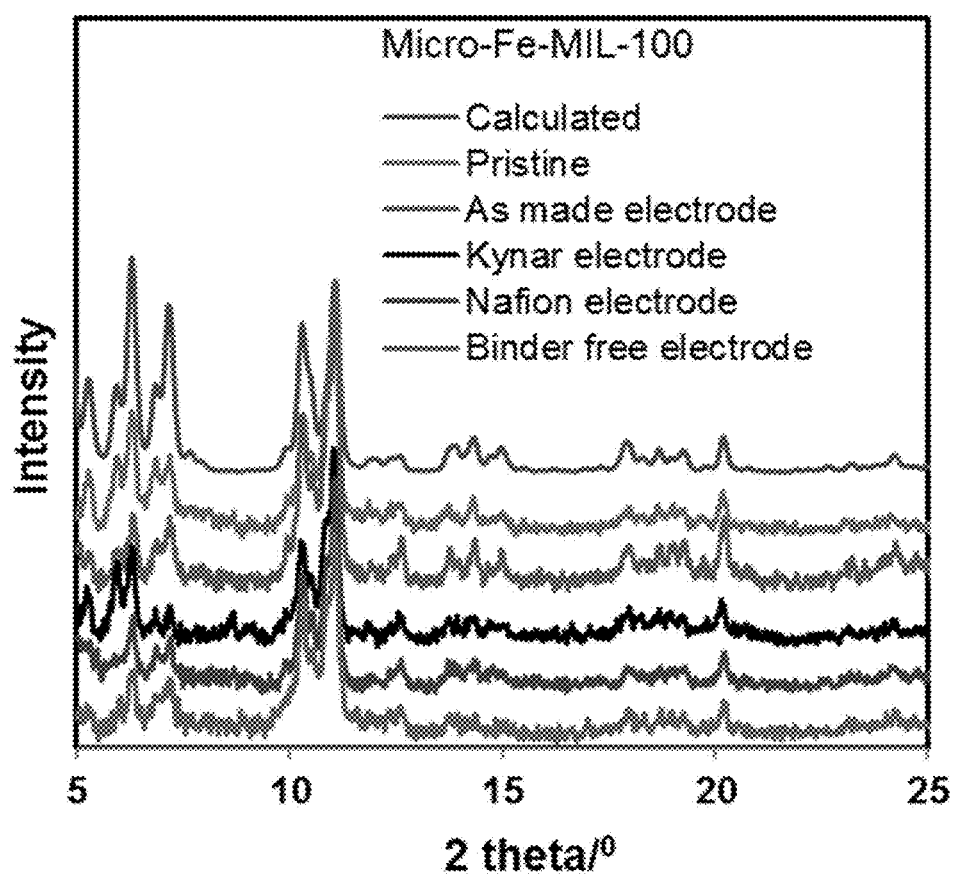
FIG. 12 is a graph of X-ray diffraction data of pristine and cycled micro-Fe-MIL-100electrodes. All Kynar, Nafion, and binder-free electrodes were characterized in their desodiated state, after 30 cycles.
Figures 13A, 13B:
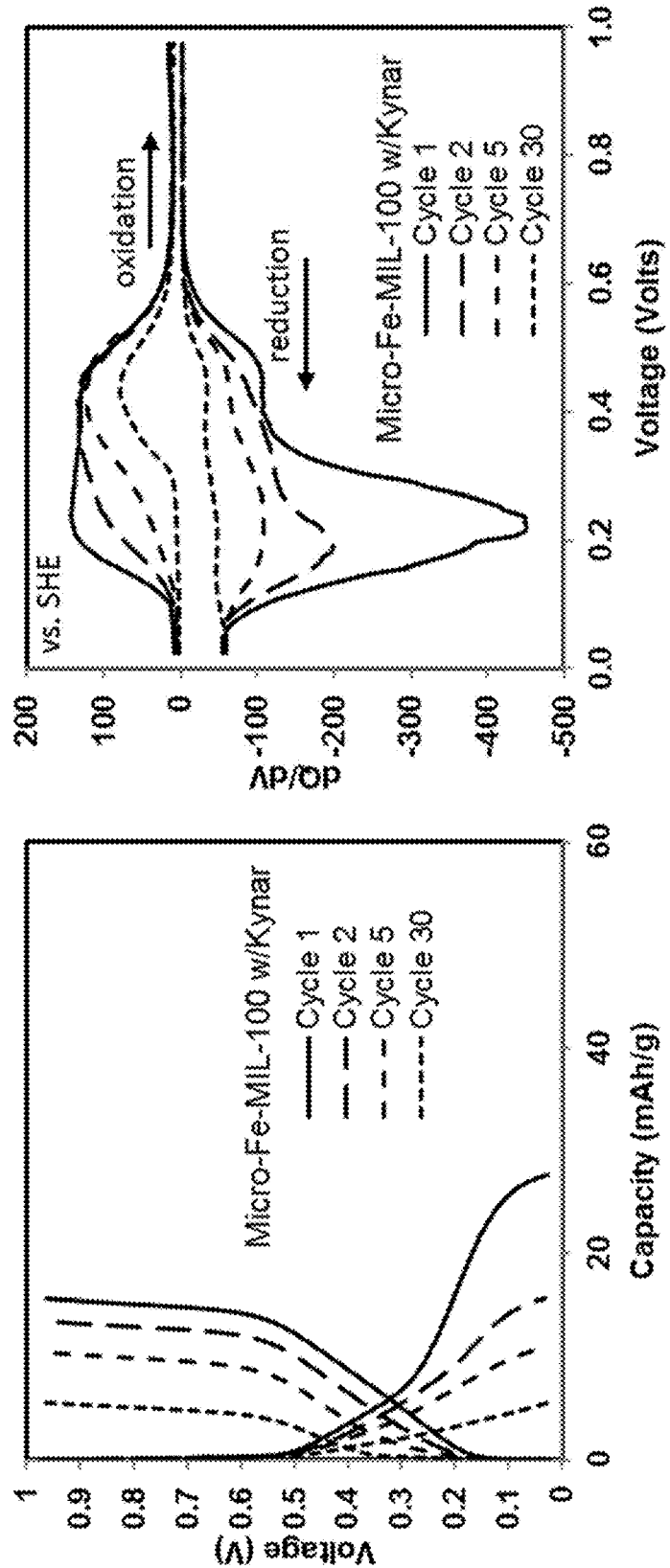
FIGS. 13(a)-(f) are graphs of voltage vs. capacity (left) and differential capacity analysis (right) for various compositions of micro-Fe-MIL-100 after the $1^{st}$, $2^{nd}$, $5^{th}$ and $30^{th}$ cycles. All cells were cycled at C/3 in 0.05 M NaCl/water electrolyte.
Figure 13D:
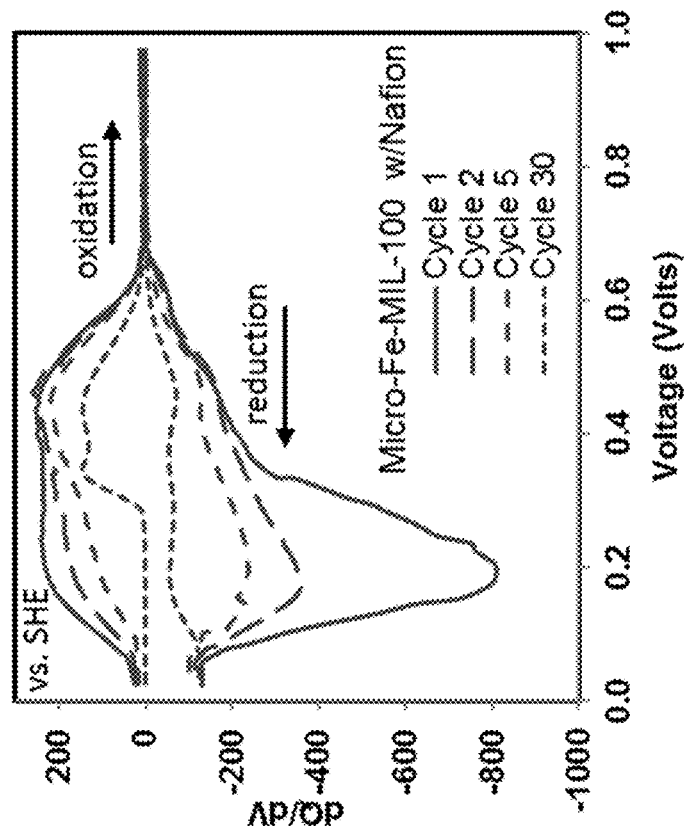
Figure 13C:
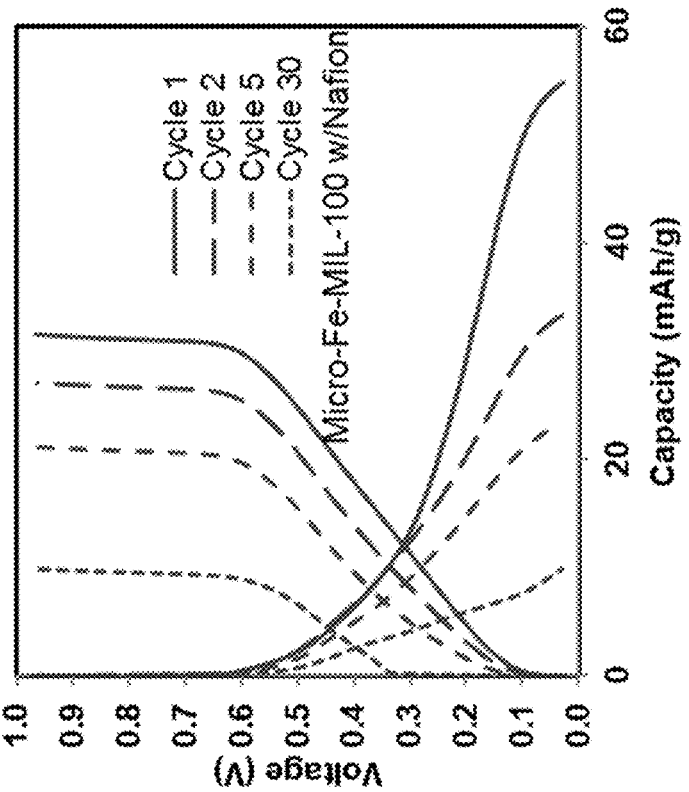
Figure 13F:
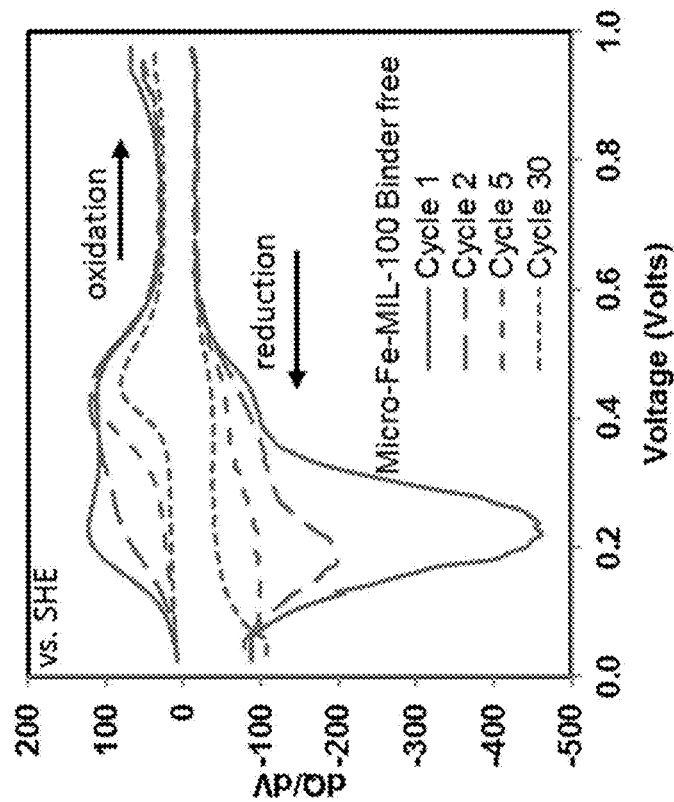
Figure 13E:
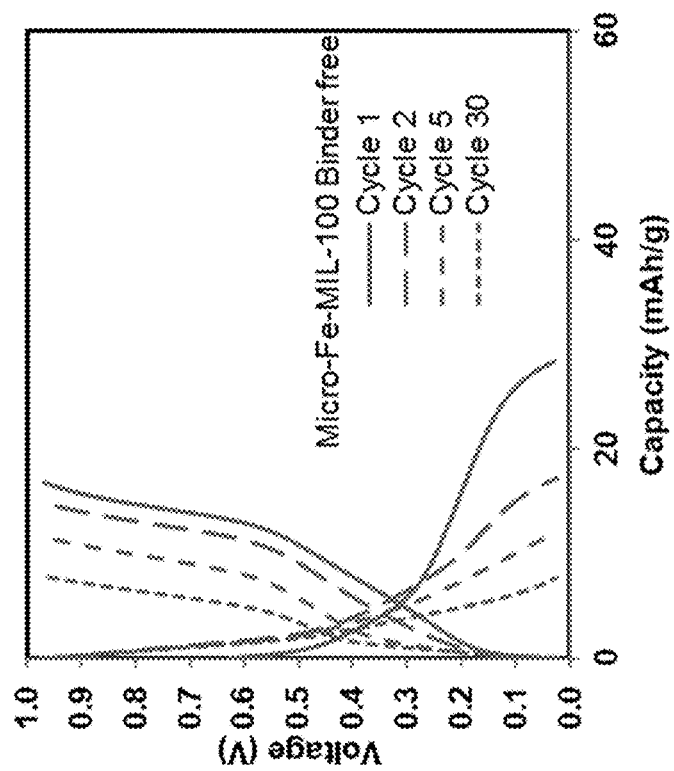

Powder X-ray diffraction analyses were conducted on all cycled electrodes to assess whether the decline in performance is related to a change in the crystalline structure of Fe-MIL-100. FIG. 12 shows that the structure of micro-Fe-MIL-100 is mainly preserved and does not undergo any drastic structural changes under electrochemical activity. Similar behavior was observed for nano-Fe-MIL-100. Additionally, no new crystalline or amorphous phases are noted.

To better understand the cycle life behavior shown in FIGS. 10(a) and 10(b), voltage profiles as functions of capacity and differential capacity (dQ/dV) for all compositions are presented in FIGS. 13(a)-(f) for $1^{st}$, $2^{nd}$, $5^{th}$, and $30^{th}$ cycle. Consistent with the CV data, the first cycle data shows that the bulk of the capacity during both reduction and oxidation occurs between ~0.1 and ~0.6 V. Highly sloping capacity plateaus are expected based on the wide CV peaks, rather than the flat plateaus that normally relate with sharp peaks. The sloping plateaus largely exhibit capacity between ~0.1 and ~0.3 V during first cycle reduction, consistent with the largest reduction peaks shown in the CV. Capacity in this potential range is referred to as the lower potential capacity. Differences in reduction capacity between the various binder systems are largely associated with differences in capacity given by this lower potential capacity of the sloping plateau. A smaller amount of reduction capacity relates with reduction potentials between ~0.3 and ~0.6 V, which is referred to as the higher potential capacity. dQ/dV data is also consistent with the CV data for the first cycle; large reduction peaks are linked with lower potential capacity and smaller peaks are correlated with the higher potential capacity.

Upon oxidation, the capacity curves do not mirror the reduction curves during the first cycle, but rather slope almost linearly from 0.1 V to 0.6 V with reduced capacity. Again, this is consistent with the CV and the dQ/dV plots for the first cycle in which the lower potential peaks are smaller during oxidation than during reduction and the oxidation peaks in general are less distinct than during reduction. The higher potential oxidation and reduction peaks in the dQ/dV data are more comparable in magnitude than the lower potential oxidation peaks.

During cycles 2, 5 and 30, the lower potential sloping plateau disappears and the related reduction peaks in the dQ/dV data decrease greatly in magnitude. This decrease is accompanied by an increase in the CE but a decrease in overall capacity, as shown in FIGS. 10(a) and 10(b). The higher potential capacity remains more consistent with cycling as compared to the lower potential capacity. Also, the magnitudes of the oxidation and reduction peaks are similar in the high potential capacity regime. The corresponding data (not shown) for the nano-Fe-MIL-100 show very similar behavior as micro-Fe-MIL-100.

The enhanced capacity in the first cycles is largely associated with the lower potential sloping plateau shown in FIGS. 13(a)-(f) and the lower potential peaks shown in the CV and dQ/dV, FIGS. 9(a)-(b) and FIGS. 13(a)-(f). With cycling, the low potential electrochemical activity is greatly reduced and the Nafion-bound system becomes more comparable to the other systems. All binder systems exhibit significant capacity fade with cycling and the binder is shown to have little effect by the 30th cycle.

The same phenomenon is frequently encountered in organic electrolyte systems and is often attributed to electrolyte breakdown with concomitant formation of a solid electrolyte interphase (SEI) in early cycles. However, in aqueous electrolytes, the breakdown products are gases ($H_2$ and $O_2$) rather than solid carbonaceous materials. Barring reaction of the active electrode material with water, $H_2$, $O_2$, or the electrolyte salt, irreversible capacity loss in early cycles is generally not attributed to SEI formation in aqueous electrolytes. See H. Kim et al., Chem. Rev. 114, 11788 (2014); and Y. Wang et al., Adv. Energy Mater. 2, 830 (2012).

Interestingly, the system shows low CE in early cycles when the capacity is the highest, while the trend is reversed in later cycles, in particular after the $20^{th}$ cycle. Examination of the multiple peaks in the CV, shown in FIGS. 9(a)-(b), and differential capacity plots, shown in FIGS. 13(a)-(f), also helps explain the trends in the cycle life and CE data. Although the first cycle in this system shows the highest initial capacity, the CE is only 60%, indicating that the first cycle is not entirely reversible, as shown in FIGS. 10(a)-(b). Contrastingly, coinciding with the rapid capacity fade is an increase in CE to nearly 100% after 20 cycles, when the capacity stabilizes. Close examination of FIGS. 9(a)-(b) and 13(a)-(f) reveals that the irreversibility in the system is largely connected with the lower potential sloping plateau capacity and the large lower potential peaks in the CV. The oxidation peaks associated with the lower potential reduction peaks are much smaller in magnitude than the reduction peaks. In contrast, the higher potential reduction peaks in the CV and dQ/dV plots are typically similar in magnitude to oxidation peaks in higher potential range. Furthermore, with greater numbers of cycles, the lower potential sloping plateau disappears (along with the corresponding peaks in the CV and dQ/dV plots) and the higher potential capacity dominates. Thus, the higher potential capacity is coupled with high CE. It is likely that the Na intercalation which occurs in the lower potential range is not very reversible, while the Na intercalation in the higher potential range is reversible. This difference in reversibility may be linked to the high and low potential activity being related to intercalation into different sites.

Figure 14A:
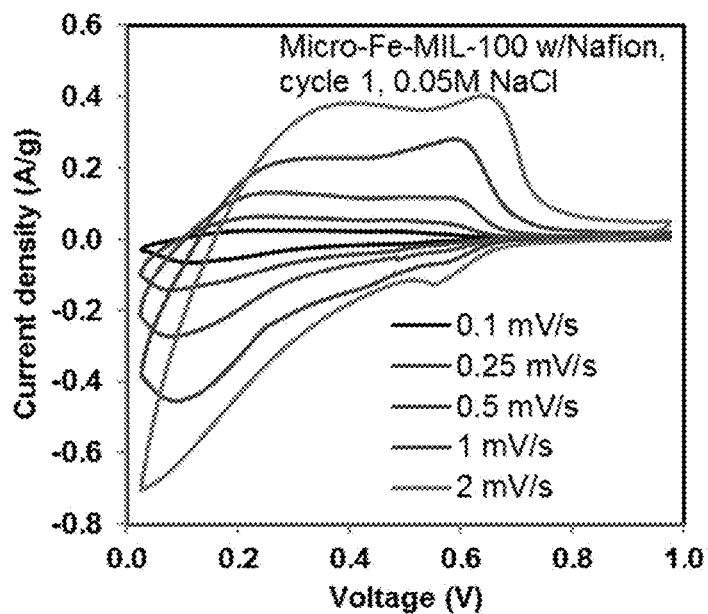
FIG. 14(a) is a graph of cyclic voltammetry analysis at variable scan rates.
Figure 14B:
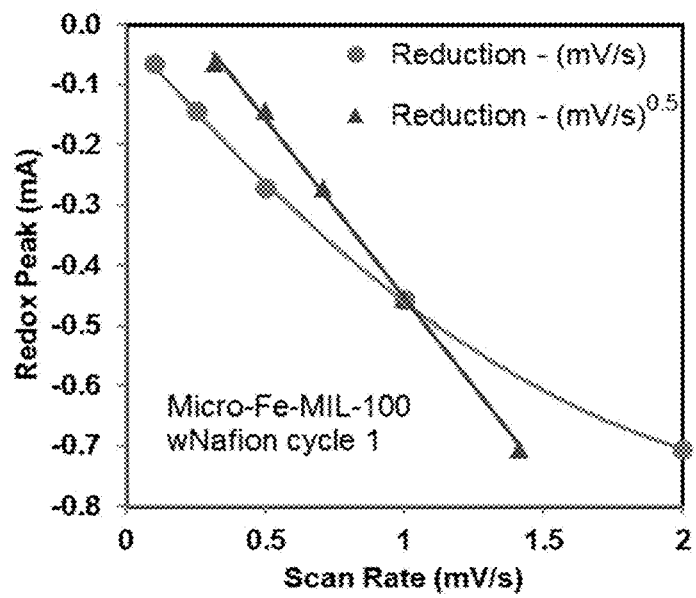
FIG. 14(b) is a graph of reduction peak current plotted against varying scan rates (0.1, 0.25, 0.5, 1, and 2 mV/s) in 0.05 M NaCl/water for micro-Fe-MIL-100 with Nafion binder.

To better understand the mechanism for sodium storage in the best performing system (micro-Fe-MIL-100 with Nafion binder), a CV analysis was performed at various scan rates (0.1, 0.25, 0.5, 1, and 2 mV/s), as shown in FIG. 14(a). The square root dependence of peak potential on scan rate shown in FIG. 14(b) indicates that charge storage is Faradaic in nature and likely is associated with an intercalation process, as previously shown with other intercalation-based battery electrodes. See H. Kim et al., Chem. Rev. 114, 11788 (2014); and S. Ren et al., Adv. Sci. 2, 1500128 (2015). The corresponding plot (not shown) for the oxidation peaks exhibits the same trend.

The complexity of the structure correlates with multiple possible Fe active sites where the Na intercalated species can be stored, as previously suggested by other studies. See D. F. Sava Gallis et al., J. Mater. Chem. A 4, 13764 (2016); and J. Shin et al., J. Mater. Chem. A 3, 4738 (2015). It is possible that some of these sites are not accessible to Na ions or not accessible to the electrons needed to undergo oxidation and reduction of the Fe species. Further evidence of multiple sites arises from the multiple broad peaks in the CV, as shown in FIGS. 9(a)-(b), and changes in slope for the capacity in the GC data, as shown in FIGS. 13(a)-(f). The changes in slope and multiple peaks suggest that there is a range of energies associated with $Na^+$ intercalation.

There are several potential reasons for irreversibility in these systems. It is possible that Na is intercalated into several sites with different energies and only some of the sites have favorable energetics for the Na to deintercalate upon oxidation. Thus, with cycling, fewer Na ions can be intercalated into those sites because many are still occupied from the previous cycle. This trapping of Na could also explain the low CE in the early cycles. Additionally, even though the counter electrode is larger in mass than the working electrode, it also likely undergoes this process slowly over its cycling life, making the electrochemical cell overall less efficient. It is also foreseeable that within a larger voltage window, these Na ions could be deintercalated. However, the voltage window studied here was limited to prevent electrolyte breakdown.

The present invention has been described as metal-organic framework electrodes for sodium ion batteries. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A sodium ion battery, comprising:
    a cathode comprising a porous redox active metal-organic framework material, wherein the metal-organic framework material comprises an iron (III) carboxylate;
    a sodium anode; and
    an ion-conductive electrolyte between the cathode and the anode;
    wherein charging of the battery causes positive sodium ions to deintercalate from the cathode and migrate through the ion-conductive electrolyte to the anode and discharging causes at least some of the sodium to reversibly migrate from the anode and intercalate back into the cathode.

2. The sodium ion battery of claim 1, wherein the iron (III) carboxylate comprises $Fe_3O(H_2O)_2(OH)[C_6H_3(CO_2)_3]_2 \cdot 12H_2O$.

3. The sodium ion battery of claim 1, wherein the cathode further comprises a binder.

4. The sodium ion battery of claim 3, wherein the binder comprises a hydrophilic binder.

5. The sodium ion battery of claim 4, wherein the hydrophilic binder comprises a sulfonated tetrafluoroethylene based fluoropolymer-copolymer or sodium carboxymethyl cellulose.

6. The sodium ion battery of claim 3, wherein the binder comprises a hydrophobic binder.

7. The sodium ion battery of claim 6 wherein the hydrophobic binder comprises hexafluoropropylene-vinylidene fluoride copolymer or polytetrafluoroethylene.

8. The sodium ion battery of claim 1, wherein the sodium anode comprises sodium metal, a sodium-based alloy, a carbon-based compound, or a titanium-based compound.

9. The sodium ion battery of claim 1, wherein the electrolyte comprises a sodium salt dissolved in an organic solvent or mixture of organic solvents.

10. The sodium ion battery of claim 9, wherein the sodium salt comprises $NaPF_6$ or $NaClO_4$.

11. The sodium ion battery of claim 9, wherein the sodium salt comprises sodium fluoride, sodium tetrafluoroborate, sodium triflate, or sodium triflimide.

12. The sodium ion battery of claim 9, wherein the organic solvent comprises propylene carbonate, ethylene carbonate, dimethyl carbonate, or dimethoxyethane.

13. The sodium ion battery of claim 1, wherein the electrolyte comprises a sodium salt dissolved in water.

14. The sodium ion battery of claim 13, wherein the sodium salt comprises a sodium halide, sodium sulfate, or sodium phosphate.

15. The sodium ion battery of claim 1, further comprising a porous separator separating the cathode from the anode that allows sodium ions to cross it.

16. The sodium ion battery of claim 1, wherein the sodium ion battery comprises a coin cell battery.

\* \* \* \* \*